United States Patent [19]

Esders et al.

[11] Patent Number: 4,547,461
[45] Date of Patent: Oct. 15, 1985

[54] COMPOSITION, ANALYTICAL ELEMENT AND METHOD FOR THE QUANTIFICATION OF CREATINE KINASE

[75] Inventors: Theodore W. Esders, Webster; Shirley Y. Lynn; John B. Findlay, both of Rochester; Richard M. Schubert, Spencerport, all of N.Y.

[73] Assignee: Eastman Kodak Company, Rochester, N.Y.

[21] Appl. No.: 459,026

[22] Filed: Jan. 18, 1983

[51] Int. Cl.$^4$ .................. C12Q 1/29; C12Q 1/50; C12Q 1/48; C12Q 1/26; C12Q 1/28; C12N 9/12; G01N 1/48; G01N 21/06

[52] U.S. Cl. .................................. 435/17; 435/15; 435/25; 435/805; 435/810; 435/28; 435/194; 422/56; 422/57

[58] Field of Search .................. 435/4, 194, 15, 25, 435/17, 805, 810, 28; 422/56, 57

[56] References Cited

U.S. PATENT DOCUMENTS

| | | | |
|---|---|---|---|
| 3,992,158 | 11/1976 | Przybylowicz et al. | 23/253 TP |
| 4,012,286 | 3/1977 | Sanderson et al. | 435/15 |
| 4,089,747 | 5/1978 | Bruschi | 195/99 |
| 4,118,279 | 10/1978 | Determann et al. | 195/63 |
| 4,166,005 | 8/1979 | Masurekar et al. | 435/190 |
| 4,241,178 | 12/1980 | Esders et al. | 435/15 |
| 4,286,057 | 8/1981 | Wulff et al. | 435/8 |
| 4,352,881 | 10/1982 | Inagawa et al. | 435/17 |

FOREIGN PATENT DOCUMENTS 60518  9/1982  European Pat. Off. ............. 435/15

OTHER PUBLICATIONS

Tietz (Ed.), *Fundamentals of Clinical Chemistry*, W. B. Saunders Co., 1970, pp. 466–470.
Scad. J. Clin. Lab. Invest. 36 (1976), pp. 711–723; Ibid. 39 (1979), pp. 1–5.
Clin. Chem. 27(3), pp. 402–404 (1981).

*Primary Examiner*—Thomas G. Wiseman
*Assistant Examiner*—Robin L. Teskin
*Attorney, Agent, or Firm*—J. Lanny Tucker

[57] ABSTRACT

An enzymatic method for the analytical determination of creatine kinase in an aqueous liquid such as blood serum is described. The determination is made by measuring an optical density change using the reagents creatine phosphate, adenosine diphosphate, glycerol, glycerol kinase, α-glycerophosphate oxidase, a chromagen and a mercapto-containing creatine kinase activator. The mercapto-containing creatine kinase activator is added in encapsulated form or in low concentrations so as to preserve the activity of the chromagen.

26 Claims, 2 Drawing Figures

COMPOSITION, ANALYTICAL ELEMENT AND METHOD FOR THE QUANTIFICATION OF CREATINE KINASE

FIELD OF THE INVENTION

The present invention relates to the analysis of aqueous liquids for creatine kinase content. More specifically, it relates to a reagent composition, an analytical element and an improved method for assaying biological fluids, e.g. blood serum, for creatine kinase.

BACKGROUND OF THE INVENTION

Determination of the presence and quantity of creatine kinase in biological fluids, particularly in human blood serum, has become very useful in the diagnosis of myocardial infarctions.

Conventional procedures for creatine kinase determination generally involve the consideration that creatine kinase catalyzes both the forward and reverse reactions illustrated by the equation:

creatine + adenosine triphosphate ⇌ creatine phosphate + adenosine diphosphate. Both the forward and reverse reactions have been used in analytical procedures, but use of the reverse reaction is preferred because it is about 6 times faster than the forward reaction.

In one known analytical procedure carried out in solution, creatine and adenosine triphosphate (hereinafter ATP) are incubated with the liquid sample to be assayed. After a suitable time, the conversion of creatine to creatine phosphate is stopped by adding an acid to the sample. The acid hydrolyzes only the creatine phosphate to provide free inorganic phosphate which is measured colorimetrically as a directly proportional measure of creatine kinase activity. This procedure, while providing a simple and direct measure of creatine kinase activity, requires both an undesirably large sample volume to obtain a measurable amount of phosphate and unacceptable incubation times (e.g. up to 1 hour). Because of the strong reverse reaction of the equation hereinabove, adenosine diphosphate (hereinafter ADP) begins to inhibit the forward reaction as its concentration increases over the long incubation time. Further, this procedure does not allow for continuous kinetic monitoring of creatine kinase.

Other known procedures for measuring creatine kinase in solution involve coupling two or more enzyme reactions together as described, for example, in N. W. Tietz (Ed.), *Fundamentals of Clinical Chemistry*, W. B. Saunders Co., 1970, pp. 466–470. One measurement technique described in that reference is illustrated on page 467 in equations 45a–45c. The desired measurable product of the reaction sequence is nicotinamide adenine dinucleotide phosphate (reduced form, hereinafter NADPH) the presence of which is measured at 340 nm with a spectrophotometer. This procedure, however, is extremely pH-sensitive and subject to considerable error if strict pH control is not maintained. Further, NADPH and NADP+ (oxidized form) are relatively unstable. It would be desirable to avoid UV assay procedures because they require relatively complicated instrumentation and are subject to interferences from various serum components when creatine kinase activity is measured.

It is also known that creatine kinase is unstable in biological fluids apparently due to sulfhydryl (i.e. mercapto) oxidation and disulfide formation. Hence, an activator is commonly employed in solution assays to restore full creatine kinase activity. Sulfhydryl compounds such as thioglucose, dithiothreitol, dithioerythritol, mercaptoethanol, N-acetylcysteine and glutathione are among the most common activators used in the analytical procedures known in the art, e.g. procedures wherein changes in UV absorbance are measured. However, although it would be highly desirable to use colorimetric assay procedures, it has been found that when activators are used in high enough concentrations for desired creatine kinase activation, they adversely affect many chromogens (also known as colorimetric indicators) useful in colorimetric assays. Generally, the activators bleach such chromogens so that the color density is reduced and the assay then becomes unreliable.

For example, in U.S. Pat. Nos. 4,241,178 (issued Dec. 23, 1980 to Esders et al); and 4,089,747 (issued May 16, 1978 to Bruschi) a colorimetric assay method for measuring glycerol and a composition for detecting hydrogen peroxide, respectively, are described. The detectable colorimetric changes brought about by the described method are obtained from the use of chromogens (e.g. dyes, dye precursors, dye formers etc.) which can provide color changes when reacted with a peroxide. But it has been found that the chromogens described therein are undesirably bleached when used with the mercapto-containing activators noted hereinabove at concentrations generally required in known solution assays.

Hence, there is a need for a colorimetric method for determining creatine kinase in aqueous fluids which method avoids the disadvantages of known methods. Such disadvantages include the need for large volume samples for carrying out assay procedures. A colorimetric method is also desired which utilizes a reaction sequence involving stable reagents and byproducts which provides detectable and reproducible colorimetric changes, thereby avoiding the problems presented by known UV assay procedures. It is further desired that such a method be suitable for both solution and dry assay procedures.

SUMMARY OF THE INVENTION

The present invention provides a composition, an analytical element and a method for the quantification of creatine kinase in aqueous liquids. This invention overcomes the problems inherent with known creatine kinase assay procedures.

In particular, the present invention has many advantages over those known procedures. First of all, it provides reliable and precise analysis of creatine kinase through color changes measurable at one of several wavelengths in the visible region of the electromagnetic spectrum (generally between 400 and 900 mm). These measurements made in the visible region are less subject to interferences from serum components, particularly if made at higher wavelengths (e.g. greater than 500 nm) than UV measurements made at lower wavelengths (e.g. below 400 nm).

Secondly, the creatine kinase activator is present in the composition of this invention such that it is substantially inert to the colorimetric indicator composition used therein. For example, in the solution assay, by using activators at low concentrations, the stability of creatine kinase is maintained while interference with the chromogen is substantially prevented. In the dry analytical element, the creatine kinase activator can be used in a location or form such that the use of relatively high activator concentrations in such elements is facilitated. It has been unexpectedly found that a certain mercapto-containing activator, i.e. N-acetylcysteine, adequately activates creatine kinase in dry elements to provide accurate and reproducible results while simultaneously exhibiting negligible interference with the chromogen. Preincubation steps are also avoided with use of the dry element of this invention.

The stability of NADP+ and NADPH is not a concern in the present invention because a reaction sequence is employed in this invention which avoids the use of those materials. Further, the present invention allows the assay of aqueous liquids (e.g. blood serum) in either solution or dry formats using small liquid samples. Finally, the enzymes used in the practice of this invention are active over a relatively wide pH range. Thus, stringent pH control is unnecessary.

In accordance with this invention, a composition for the quantification of creatine kinase in an aqueous liquid comprises creatine phosphate, adenosine diphosphate, glycerol, glycerol kinase, $\alpha$-glycerophosphate oxidase, a colorimetric indicator composition comprising a chromogen, and a creatine kinase activator which is present such that it is substantially inert to the colorimetric indicator composition.

This invention also provides an analytical element for detecting creatine kinase. This element comprises creatine phosphate, adenosine diphosphate, glycerol, glycerol kinase, $\alpha$-glycerophosphate oxidase, a colorimetric indicator composition comprising a chromogen, and a creatine kinase activator which is present such that it is substantially inert to the colorimetric indicator composition. In a preferred embodiment, this element includes a support and, in fluid contact, first and second zones, wherein the colorimetric indicator composition is in the first zone and the activator is in the second zone.

This invention further provides a method for the quantification of creatine kinase in an aqueous liquid. This method comprises the steps of:
(A) contacting (1) a sample of the liquid, and (2) reagents which effect in the presence of a creatine kinase-containing liquid an ordered sequence of reactions wherein:
  (a) creatine phosphate and adenosine diphosphate react in the presence of creatine kinase to form creatine and adenosine triphosphate;
  (b) glycerol is phosphorylated in the presence of glycerol kinase and adenosine triphosphate to form L-$\alpha$-glycerophosphate; and
  (c) L-$\alpha$-glycerophosphate is oxidized in the presence of $\alpha$-glycerophosphate oxidase to produce an optical density change; and
(B) quantitatively detecting the rate of that optical density change.

BRIEF DESCRIPTION OF THE DRAWINGS

Both

DETAILED DESCRIPTION OF THE INVENTION

Figure 2:
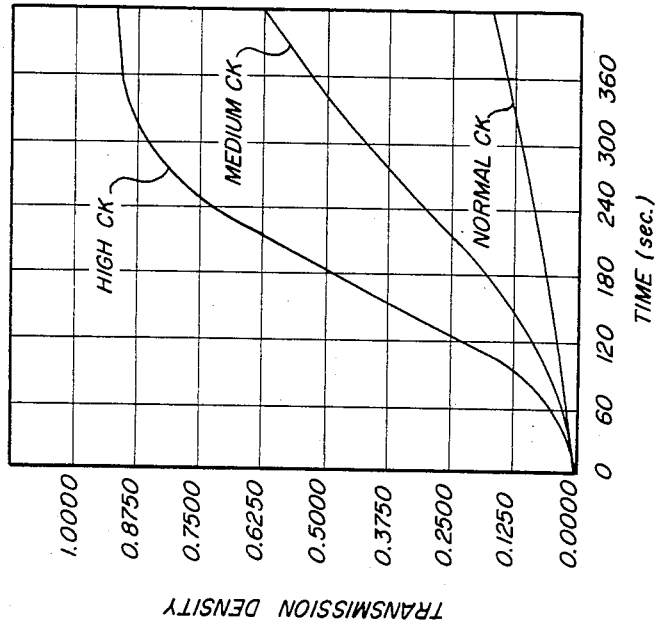
FIGS. 1 and 2 are graphs of creatine kinase activity over time, at three creatine kinase concentration levels, measured using dry analytical elements without and with a creatine kinase activator, respectively. They are discussed more fully in Example 9 hereinbelow.

The present invention relates to the quantification of creatine kinase in aqueous liquids. The practice of this invention can be accomplished with biological fluids, e.g. whole blood, plasma, sera, lymph, bile, urine, spinal fluid, sputum, sweat and the like as well as stool secretions of humans or animals. It is possible also to use fluid preparations of human or animal tissue such as skeletal muscle, heart, kidney, lungs, brains, bone marrow, skin and the like. The preferred biological fluid for practice of the invention is human blood serum. The serum in most cases need not be diluted, but can be diluted for optimum results if the amount of creatine kinase is unusually high as in the serum of a patient suffering from an acute myocardial infarct. The serum can be diluted with high protein solutions such as heated human or animal sera.

In the practice of the present invention, creatine kinase (CK) activity is preferably measured by the following sequence of reactions:

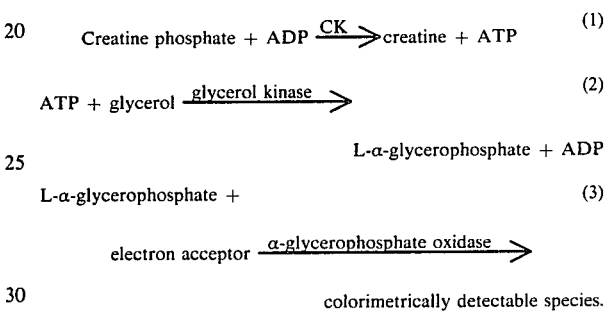

In these combined reactions, the rate of formation of the colorimetrically detectable species is directly proportional to the rate of creatine kinase activity in the liquid sample.

Although the discussion hereinafter will relate to both analytical solutions and dry analytical elements, it should be readily apparent to the skilled artisan that all of the reagents can be provided in dry form and reconstituted with water immediately prior to use. Compositions of this type are clearly contemplated hereby.

The first reaction in the above-described sequence is the reaction of creatine phosphate and ADP to form creatine and ATP in the presence of creatine kinase in the aqueous liquid sample. As is well known in the art, this reaction usually proceeds in the presence of an enzyme cofactor, such as a divalent metal ion. Exemplary cofactors are described hereinbelow. Creatine phosphate is a biological compound commercially available from any of a number of sources including Calbiochem (located in La Jolla, Calif.). ADP is the hydrolyzed form of the nucleotide ATP. ADP is readily available from a number of commercial sources, e.g. Sigma Chemical Co. (located in St. Louis, Mo.).

As shown in reaction (2) above, glycerol kinase catalyzes the phosphorylation of glycerol to L-$\alpha$-glycerophosphate in the presence in ATP. Generally, any glycerol kinase is useful in the successful practice of the present invention although those obtained from *E. coli* and *Candida mycoderma* are preferred. Glycerol kinase enzymes from other sources are well known in the art. A complete discussion of such materials and further references to their preparation and reactivity may be found in T. E. Barman, *Enzyme Handbook*, I, Springer-Verlag, N.Y. (1969) pages 401–402. Worthington Biochemical Company (located in Freehold, N.J.) is a commercial source of glycerol kinase.

The glycerol useful in the composition of this invention can also be readily obtained commercially from, e.g. Eastman Organic Chemicals (located in Kingsport, Tenn.) or prepared using techniques well known in the art. Glycerol can be provided either in free form or as a fatty acid ester of glycerol (e.g. triglycerides). Preferably, free glycerol is used in the practice of this invention.

The next step in the reaction sequence involves the oxidation of L-α-glycerophosphate in the presence of L-α-glycerophosphate oxidase and, generally, an electron acceptor to produce a colorimetrically detectable species. This species is quantitatively related to the creatine kinase contained in the liquid sample.

L-α-glycerophosphate oxidase is a microbial enzyme which can be derived from a variety of sources. A detailed description of this enzyme and exemplary sources are described in U.S. Pat. No. 4,241,178 noted hereinabove. Also, the following references describe both the enzyme and useful techniques for its preparation and extraction: Esders et al, "Purification and Properties of L-α-Glycerophosphate Oxidase from *Streptococcus faecium* ATCC 12755," J. Biol. Chem., 254, pp. 2710-2715 (1979); Koditschek et al, "α-Glycerophosphate Oxidase in *Streptococcus faecium*, F 24," Journal of Bacteriology, 98, (3), pages 1063-1068 (1969) and U.S. Pat. No. 4,166,005 (issued Aug. 28, 1979 to Masurekar et al). The enzyme can also be obtained commercially from Toyo Jozo (located in Shizuoka, Japan).

The oxidation of L-α-glycerophosphate occurs in the presence of an electron acceptor. Any electron acceptor which will permit oxidation of the phosphate by the oxidase with the concomitant production of a colorimetrically detectable species is suitable for use in this invention.

In one embodiment, the electron acceptor can be a colorimetric indicator composition containing a chromogen (which is defined in more detail hereinbelow). Such chromogen can be reduced to provide either a color change (i.e. shift in absorbance), a color where before it was colorless or a loss in color density (but not a color shift). Any of these changes could then be monitored to measure creatine kinase activity. Certain indolphenols, potassium ferricyanide and certain tetrazolium salts are useful in the practice of this embodiment. For example, 2,6-dichlorophenolindolphenol alone or in combination with phenazine methosulfate, and 2-(p-indophenyl)-3-(p-nitrophenyl)-5-phenyl-2H-tetrazolium chloride either alone or in combination with phenazine is especially useful.

In an alternative and preferred embodiment, the electron acceptor oxidizes the phosphate to produce an intermediate species which then reacts with a colorimetric indicator composition to produce a colorimetrically detectable species according to the following equations:

L-α-glycerophosphate +           (3a)

dihydroxyacetone phosphate + intermediate species (4)

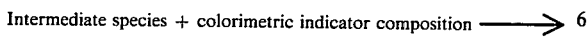

colorimetrically detectable species.

Quantification of creatine kinase in the practice of this preferred embodiment is achieved using oxygen as electron acceptor and a colorimetric indicator composition which comprises: (1) a substance having peroxidative activity, and (2) a chromogen. Reaction (3a) produces reaction products of dihydroxyacetone phosphate and hydrogen peroxide.

Colorimetric indicator compositions useful to react with hydrogen peroxide in equation (4) are well known in the art. Generally, such compositions comprise a substance which has peroxidative activity. Preferably, this substance is peroxidase.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase). It also occurs in microorganisms and can be produced by fermentation. Certain synthetic peroxidases, such as those disclosed by Theorell and Meahly in Acta Chem. Scand., Vol. 4, pages 422-434 (1950), are also useful. A preferred peroxidase is that obtained from horseradish.

Also useful but to a lesser extent are such substances as hemin, methemoglobin, oxyhemoglobin, hemoglobin, hemochromogen, alkaline hematin, hemin derivatives, iron sulfocyanate, iron tannate, ferrous ferrocyanide, chromic salts (such as potassium chromic sulfate) absorbed in silica gel, etc.

The colorimetric indicator composition also comprises a chromogen which is a colored or colorless substance which directly or indirectly provides a quantifiable colorimetric change (e.g. color, color change or color density change) which can be quantitatively measured. Such chromogen can be dyes, dye formers or dye precursors. The color provided by the reaction of the chromogen is in the visible region of the electromagnetic spectrum (i.e. between about 400 and 900 nm).

Chromogens which provide color formation in the presence of hydrogen peroxide and peroxidase which may be employed in indicator compositions useful in the present invention include (with a color coupler where necessary): monoamines, diamines, phenols, polyphenols, aromatic acids, leuco dyes, colored dyes and the like.

Other chromogens which contain a material oxidizable in the presence of peroxidase and which can provide a colorimetrically detectable species include certain dye-providing compositions. In one aspect, such chromogens can include a compound that, when oxidized by peroxidase, can couple with itself or with its reduced form to provide a dye. Such autocoupling compounds include a variety of hydroxylated compounds which are well known in the art.

In another aspect, the detectable species can be provided by chromogens which include a peroxidase-oxidizable compound capable of undergoing oxidative condensation with couplers such as those containing phenolic groups or activated methylene groups, together with such a coupler. Representative of such oxidizable compounds are benzidene and its homologs, p-phenylenediamines, p-aminophenols, 4-aminoantipyrine, etc. A wide range of such couplers, including a number of autocoupling compounds, is described in the art, such as in *The Theory of the Photographic Process* Mees and James (Eds), (1966), Chapter 17; Kosar,

*Light-Sensitive Systems,* 1965, pages 215-249 and U.S. Pat. No. 4,321,397 (issued Mar. 23, 1982 to Nix et al).

In still another and preferred aspect, the colorimetrically detectable species can be provided by peroxidase-induced oxidation of a leuco dye to provide the corresponding dyestuff form.

A variety of leuco dyes are useful as chromogens in the practice of this invention including those described in U.S. Pat. Nos. 4,241,178 and 4,089,747 both noted hereinabove, the disclosures of which are incorporated herein by reference.

Leuco dyes preferred for use in this invention are the triarylimidazoles of U.S. Pat. No. 4,089,747. These dyes generally are of the formula

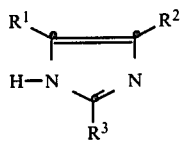

wherein each of $R^1$, $R^2$ and $R^3$ is an organic group such that at least one of them is an ortho or para hydroxy-substituted aryl group of up to 18 carbon atoms. The other two radicals are chosen such that the oxidation potential of the imidazole lies between about $-70$ mV to about $+110$ mV as measured by cyclic voltometry against a standard calomel electrode using a carbon based electrode. As used herein, aryl is meant to include aromatic hydrocarbon groups (e.g. phenyl, naphthyl, etc. including substituted aromatic groups). The total number of carbon atoms refers to the number of carbon atoms in the aromatic group including substituents. Further details of useful triarylimidazoles and their preparation are described in U.S. Pat. No. 4,089,747 and references mentioned therein.

Particularly useful leuco dyes include 2(3,5-dimethoxy-4-hydroxyphenyl)-4,5-bis(4-dimethylaminophenyl)imidazole, 2-(4-hydroxy-3-methoxyphenyl)-4,5-bis(p-dimethylaminophenyl)-1H-imidazole and 2-(3-ethoxy-4-hydroxyphenyl-4,5-bis(p-dimethylaminophenyl)-1H-imidazole.

As is well known in the art, leuco dyes are often used with a color coupler compound in order to provide the desired color. When used together, it is also known that the dye and color coupler must be appropriately matched in the particularly buffered medium to provide desired results. Typical color couplers useful in the practice of this invention include phenol, naphthol, aromatic amine or reactive methylene couplers. Some leuco dyes can be used without color couplers.

duced, the assay procedure used etc., and are readily determinable by the skilled artisan. Typical values are shown in Tables I and II below.

The novel assay compositions of this invention also contain one or more creatine kinase activators which promote full creatine kinase activity. These activators are present in the composition such that they are substantially inert to the colorimetric indicator composition. In other words, the activators are present in either a concentration (or coverage), location (e.g. in dry elements) or form (e.g. encapsulated) such that they are substantially inert to the colorimetric indicator composition. For example, in the solution assay procedure, the activators are present in concentrations low enough so as not to interfere (i.e. react or catalyze reactions) with any of the components of the colorimetric indicator composition (i.e. the peroxidative substance, e.g. peroxidase, or the chromogen, e.g. leuco dye). Such interference is usually exhibited by undesirable bleaching of the chromogen. In the element, placement of the activator can be used to avoid interferences. It was surprising to discover that one could use high concentrations of activator in dry assay procedures and still avoid dye bleaching.

Although a variety of compounds are known to activate creatine kinase in enzymatic reactions, particularly useful activators are mercapto-containing compounds (also known as thiol-containing or sulfhydryl compounds), such as thioglucose, dithiothreitol, dithioerythritol, mercaptoethanol, glutathione, N-acetylcysteine, cysteine, thioglycerol and thioglycolic acid. A preferred activator, for both solution and dry assay procedures, is N-acetylcysteine.

In solution assay procedures, the final assay solution concentration of the activator is quite important. In the practice of this invention in solution assays, the activator is present in an amount of less than about 0.2 mM and preferably in an amount of from about 0.05 to about 0.15 mM as measured in the final assay solution.

The concentration of the other components of the novel compositions described herein can be varied broadly depending upon the liquid sample under assay (i.e. blood serum, diluted or undiluted, or other complex aqueous solution). Table I below provides a ready reference for the generally useful and preferred concentration ranges of the other essential reagents of the novel assay compositions of this invention when used in solution assays. These concentrations are measured in the final assay solution. Additional reagents (e.g. enzymes, cofactors, solvents, adenylate kinase inhibitors, etc.) can be included in the solution if desired, as is known in the art.

TABLE I

| Enzyme | Generally useful range | Preferred range |
|---|---|---|
| glycerol kinase | 0.05-1 U/mL | 0.2-0.8 U/mL |
| α-glycerophosphate oxidase | 1-30 U/mL | 8-20 U/mL |
| peroxidative substance (e.g. peroxidase) | 0.20-2 U/mL | 0.24-1.4 U/mL |
| creatine phosphate | 5-80 μ moles/mL | 20-50 μ moles/mL |
| ADP | 0.5-5 μ moles/mL | 1-4 μ moles/mL |
| glycerol | 1-20 μ moles/mL | 3-8 μ moles/mL |
| chromogen (e.g. leuco dye) | 0.03-0.4 μ moles/mL | 0.06-0.2 μ moles/mL |

The concentrations of the components of the colorimetric indicator compositions useful in the practice of this invention are dependent to a large extent upon the concentration of creatine kinase in the sample, the sophistication of the detection apparatus, the dye produced, Of course, useful results can be obtained outside of these ranges. However, these have generally been found particularly useful and preferred as indicated. Throughout this specification, one international unit of enzyme is defined as that quantity of enzyme which results in the conversion of one micromole of substance in one minute under standard assay conditions.

As is well recognized in the art, each of the enzymes used in the practice of this invention possesses a pH-activity profile, i.e. the activity of the enzyme varies with pH. Although not wishing to be so limited, it is desirable to buffer the assay compositions of this invention at a pH of between about 6.0 and about 9.0 and preferably between about 6.5 and about 7.5. Techniques and buffers for achieving this are well known in the art.

The method and composition of this invention are adaptable to both solution and dry element assays. Thus, a solution containing the described reagent composition and a suitable solvent (e.g. acetone) is prepared and creatine kinase is readily determined in an aqueous liquid by adding a sample of the liquid to a predetermined volume of the composition. The rate of color development is then monitored generally at 37° C. with a conventional spectrophotometer. This solution assay procedure is described in more detail below in Example 1.

Alternatively and preferably, the reagent composition is included in a dry analytical element, such as that described in U.S. Pat. No. 3,992,158 (issued Nov. 16, 1976 to Przybylowicz et al), the disclosure of which is incorporated herein by reference. The amount of creatine kinase is then determined by contacting (e.g. spotting) the element with the creatine kinase-containing sample. The rate of color change in one of the element zones is then directly related to the rate of ATP formation which in turn is directly related to rate of creatine kinase activity in the sample.

The analytical element of this invention generally has at least one zone containing the reagents of the composition of this invention. In this element, the creatine kinase activator can be present either in a concentration, location or form (e.g. encapsulated) such that it is substantially inert to the colorimetric indicator composition. The element preferably includes a support and a plurality (at least a first and second) of zones, each zone having certain reagents therein. Preferably, the first zone is adjacent the support. These zones are in fluid contact with each other, meaning that fluids can pass between superposed regions of adjacent zones. Stated in another manner, fluid contact refers to the ability to transport components of a fluid between the zones in fluid contact. Preferably, the zones are separate coated layers, although one or more zones can be in a single layer of an element. Typical dry element formats are known in the art and described, for example, in U.S. Pat. No. 3,992,158 noted hereinabove; as well as in U.S. Pat. Nos. 4,042,335 (issued Aug. 16, 1977 to Clément); 4,144,306 (issued Mar. 13, 1979 to Figueras); 4,132,528 (issued Jan. 2, 1979 to Eikenberry et al); 4,050,898 (issued Sept. 27, 1977 to Goffee et al); and Re. 30,267 (reissued May 6, 1980 to Bruschi).

The support for the element can be composed of any dimensionally stable material (e.g. poly(ethylene terephthalate) and is preferably transparent.

In the analytical elements of this invention, the creatine kinase activator can be unexpectedly used in much greater amounts than is used in the solution assay procedure. For example, in the element, the activator can be present in a coverage of up to about 2 g/m$^2$ (i.e. up to 130 mM), and preferably from about 0.15 to about 1 g/m$^2$ (i.e. 10–65 mM).

It is desirable in the practice of this invention that the activator and the colorimetric indicator composition be located in different zones of the element so that the color resulting from the activity of creatine kinase is not diminished by the activator. Preferably, the colorimetric indicator composition is located in the first zone and the activator is located in the second zone. One or more other zones (e.g. reagent, subbing, spreading, barrier zones) can also be in the element, such as between the first and second zones.

It has been unexpectedly found that not every known mercapto-containing activator is useful in the elements of this invention. As demonstrated in Examples 3–8 hereinbelow, several activators are useful to activate creatine kinase to some degree. Others, e.g. thioglucose, activate the kinase moderately and exhibit negligible interference with the chromogen (e.g. dye bleaching). However, only N-acetylcysteine has been observed to provide both especially high activation capability while exhibiting negligible interference with the chromogen.

Materials and elements which are adapted to use the composition of this invention are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,993,594, 3,936,357, 4,270,920, 4,248,829, 4,255,384, 4,256,693, U.K. Pat. No. 2,052,057 and *Research Disclosure*, Vol. 146, June 1976, Item 14638.

In a preferred embodiment of this invention, the element includes a support having thereon, in order from the support and in fluid contact with each other, the following zones:

a registration zone containing α-glycerophosphate oxidase and a colorimetric indicator composition comprising a substance having peroxidative activity and a chromogen;

a reagent zone containing creatine phosphate, adenosine diphosphate, glycerol and glycerol kinase; and an isotropically porous spreading zone containing a creatine kinase activator.

One or more of the zones of the elements of this invention can contain a variety of other desirable, but optional, components, including buffers, surfactants, binders (typically hydrophilic), adenylate kinase inhibitors, solvents, enzyme cofactors and chelators as are known in the art. For example, enzyme cofactors (generally divalent metal ions, e.g. $Mg^{++}$, $Mn^{++}$, $Ca^{++}$, $Fe^{++}$, $Ba^{++}$, $Sr^{++}$, $Co^{++}$, etc.) are optionally used to facilitate enzyme activity. Further, it is often desired to use adenylate kinase inhibitors (e.g. sodium fluoride, adenosine monophosphate and diadenosine pentaphosphate) in creatine kinase assays if the liquid to be assayed contains adenylate kinase. Such use, however, is optional in the practice of this invention. Further details of the elements, and particularly suitable components of the spreading zones, are given in U.S. Pat. Nos. 3,992,158 noted hereinabove and 4,258,001 (issued Mar. 24, 1981 to Pierce et al) and U.K. patent application 2,052,057 (published Jan. 21, 1981). The spreading zones, for example can be composed of either fibrous or non-fibrous materials, or both. An exemplary analytical element is illustrated hereinbelow in Example 2.

The coverage of reagents in the analytical elements of this invention can be varied broadly depending upon the liquid to be assayed. Table II below provides a ready reference for the generally useful and preferred coverages of the essential reagents although other coverages may be useful.

TABLE II

| Reagent | Generally useful coverage | Preferred coverage |
| --- | --- | --- |
| glycerol kinase | at least 400 U/m$^2$ | 1000–8000 U/m$^2$ |
| α-glycerophosphate oxidase | at least 300 U/m$^2$ | 500–5000 U/m$^2$ |
| peroxidative substance (e.g. peroxidase) | at least 1000 U/m$^2$ | 5000–50,000 U/m$^2$ |
| creatine phosphate | 0.25–10 g/m$^2$ | 0.8–5 g/m$^2$ |
| ADP | 0.02–2 g/m$^2$ | 0.1–1 g/m$^2$ |
| glycerol | 0.05–2 g/m$^2$ | 0.1–1 g/m$^2$ |
| chromogen (e.g. leuco dye) | 0.02–2 g/m$^2$ | 0.1–1 g/m$^2$ |

The following examples are provided to illustrate the practice of this invention.

EXAMPLE 1

Solution Assay Procedure

The following procedure was employed in using the composition and method of this invention. Activity of creatine kinase was measured in a solution assay using a known UV reaction scheme as well as the novel colorimetric reaction scheme described herein in order to compare results obtained from both methods.

A series of calibrator liquid samples were prepared by adding five different amounts (90, 167, 207, 284 and 318 U/L) of commercially-available rabbit muscle creatine kinase to human serum obtained from a local medical facility. About 500 μL of each calibrator sample was preincubated after the addition of about 10 mM of the activator thioglucose generally for 5–10 minutes in order to activate the creatine kinase. The samples were then cooled with ice until used.

A colorimetric indicator composition was prepared having the following components:

2.8 mg of the triarylimidazole leuco dye 2-(3,5-dimethoxy-4-hydroxyphenyl)-4,5-bis(4-dimethylam inophenyl)imidazole;

1.26 mg horseradish peroxidase;

500 μL reagent grade acetone as solvent;

0.1% Triton TM X-100 surfactant (available from Rohm & Haas, located in Philadelphia, Pa.); and 0.1M imidazole acetate buffer (at pH 7.0) sufficient to bring the final indicator composition volume to 50 mL.

A reagent mixture was prepared having the following components in 0.1 mL:

5 μmoles glycerol;

5 μmoles magnesium chloride (cofactor);

2 μmoles ADP;

35 μmoles creatine phosphate;

0.39 U glycerol kinase;

5 μmoles adenosine monophosphate (adenylate kinase activity inhibitor);

0.02 μmoles diadenosine pentaphosphate (adenylate kinase activity inhibitor); and 12 U α-glycerophosphate oxidase.

Serum was preincubated with 10 mM thioglucose for at least 5 minutes to reactivate the creatine kinase. The activity of creatine kinase in each activated serum sample was then measured in the following manner.

Approximately 0.9 mL of the colorimetric indicator composition was briefly preincubated with 0.1 mL of the reagent mixture at 37° C. in each of five cuvettes until no further background absorbance at 640 nm was observed on the spectrophotometer. About 10 μL of each activated serum sample was then added to each cuvette to initiate the reaction and the rate of color development at 640 nm was measured with a Beckman Model 25 spectrophotometer. The final concentration of creatine kinase activator in each cuvette was about 0.1 mM.

The activity of creatine kinase in each serum sample was similarly measured using a known reaction sequence resulting in ultraviolet light detection at 340 nm. This reference measurement of creatine kinase activity was accomplished by adding 10 μL of each activated serum sample to a reagent mixture in the creatine kinase Max-Pack TM kit commercially available from Calbiochem (located in La Jolla, Calif.). Again, the Beckman Model 25 spectrophotometer was used to measure absorbances. This UV assay utilizes a known reaction sequence, namely that taught in the Tietz reference, page 467, reactions 45a–45c noted hereinabove.

A calibration curve prepared using data obtained from the UV reference measurement and the colorimetric measurement was linear throughout the entire calibrator range. A linear regression between the two methods gave a slope of 0.99, indicating that the method of this invention determines creatine kinase concentration in liquid samples reliably.

Six replicate solution assays of each of three serum samples (having 37, 162 and 365 U/L creatine kinase concentration, respectively) were made using the colorimetric procedure described hereinabove in this example to establish the precision of the method of this invention. The results are given below in Table III.

TABLE III

| $\overline{X}$ (Mean for Six Assays) | Standard Deviation | Coefficient of Variation (COV) |
| --- | --- | --- |
| 37.01 U/L | 2.06 | 5.6% |
| 161.77 U/L | 5.42 | 3.4% |
| 365.47 U/L | 8.02 | 2.2% |

In comparison, three replicate solution assays using the UV assay procedure gave a 10% COV at the 365 U/L creatine kinase concentration. The low COV values for the colorimetric method of this invention indicate that it is a highly precise creatine kinase determination procedure.

$\overline{X}$, the standard deviation and the coefficient of variation were then determined by standard methods.

EXAMPLE 2

Dry Analytical Element

A dry analytical element was prepared according to the general description provided in U.S. Pat. No. 3,992,158 noted hereinabove, having the following structure:

| | |
| --- | --- |
| Spreading Zone | N—acetylcysteine activator (0.5 g/m$^2$) |
| | cellulose acetate binder |
| | Triton TM X-405 surfactant[1] |
| | Brij TM 98 surfactant[2] |
| | polyurethane binder |
| | titanium dioxide |
| Subbing Zone | poly(N—isopropylacrylamide) |
| Reagent Zone | gelatin binder |
| | 2-bis(2-hydroxyethyl)amino-2-(hydroxymethyl)-1,3-propanediol buffer (pH = 7) |
| | Triton TM X-200 surfactant[1] |
| | creatine phosphate (1.5 g/m$^2$) |
| | adenosine diphosphate (0.15 g/m$^2$) |
| | adenosine monophosphate |
| | glycerol (0.20 g/m$^2$) |
| | magnesium acetate |

| | | Registration Zone | diadenosine pentaphosphate glycerol kinase (4300 U/m$^2$) gelatin binder bisvinylsulfonylmethyl ether hardener 2-bis(2-hydroxyethyl)amino-2-(hydroxymethyl)-1,3-propanediol buffer (pH = 7) | kinase activity was measured at 37° C. and 670 nm as noted in Example 2. Table IV below contains the results of these measurements.

In addition, elements similarly prepared were spotted with 10 μL of hydrogen peroxide and the rate of dye bleach from the creatine kinase activator was noted by measuring the decrease in resulting density with time. These results are also given in Table IV below.

TABLE IV

| | | | Rate (D$_T$/min) | | | |
|---|---|---|---|---|---|---|
| Element | Creatine Kinase Activator | Coverage (g/m$^2$) | Normal CK Serum | Med. CK Serum | High CK Serum | Dye Bleach Rate |
| 3 | N—acetylcysteine | 0.54 | .044 | .123 | .280 | −0.004 |
| 4 | cysteine | 0.4 | .019 | .089 | .241 | −0.025 |
| 5 | thioglycerol | 0.36 | .020 | .088 | .177 | −0.005 |
| 6 | thioglycerol | 0.18 | .024 | .095 | .200 | −0.003 |
| 7 | dithioerythritol | 0.12 | .026 | .093 | .216 | −0.040 |
| 8 | dithioerythritol | 0.06 | .025 | .073 | .174 | −0.013 |

| | | Support | 5,5-dimethyl-1,3-cyclohexanedione antioxidant 2-(3,5-dimethoxy-4-hydroxyphenyl)-4,5-bis(4-dimethylaminophenyl) leuco dye (0.2 g/m$^2$) 2,4-di-n-pentylphenol solvent Alkanol ™ XC surfactant[3] Triton ™ X-200 surfactant[1] ascorbic acid oxidase peroxidase (32000 U/m$^2$) glycolic acid α-glycerophosphate oxidase (3200 U/m$^2$) poly(ethylene terephthalate) |

[1]Available from Rohm & Haas, located in Philadelphia, Penn.
[2]Available from Union Carbide, located in Chicago, Illinois.
[3]Available from DuPont, located in Wilmington, Delaware.

The N-acetylcysteine was incorporated into the spreading zone in a concentration sufficient to give 32 mM when the element was spotted with a 10 μL serum sample. No preincubation of the element was needed for the activator to activate the creatine kinase in a serum sample. Further, surprisingly, there was no interference with the chromogen by the activator present at this high concentration.

About 10 μL of human serum samples containing various amounts of creatine kinase (ranging from 7.5 to 2673 U/L) were spotted onto such elements and color densities were measured over a period of about 5 minutes at 37° C. and 670 nm with a Beckman Model 25 spectrophotometer (modified for use with dry element assays). The same samples were also assayed using a Rotochem ™ centrifugal analyzer (available from AMINCO located in Silver Spring, Md.).

A linear regression curve was plotted using the data obtained from the Rotochem ™ assay and the element of this invention. This curve had a slope of 0.984, an intercept of 5.8 U/L and an r value of 0.993, all of which indicate that the colorimetric method of this invention practiced in the element of this invention reliably and accurately determined creatine kinase activity in the human serum assayed.

EXAMPLES 3-8

Use of Various Creatine Kinase Activators

Dry analytical elements were prepared as described in Example 2 except that various creatine kinase activators were incorporated into the spreading zone. Each element was spotted with 10 μL samples from 3 human serum pools, comprising normal (45-300 U/L), medium (300-600 U/L) and high (greater than 600 U/L) creatine kinase activity, respectively. The rate of creatine It is apparent from the data in Table IV that neither of the activators, N-acetylcysteine and thioglycerol, caused significant dye bleaching in the elements of this invention. However, consistently faster rates were obtained in elements containing N-acetylcysteine. Hence, of the activators tested, N-acetylcysteine unexpectedly exhibited both high activation of creatine kinase as well as negligible interference (i.e. dye bleach) with the chromogen.

EXAMPLE 9

Elements With and Without Creatine Kinase Activator

This is a comparative example comparing the measurement of creatine kinase activity with a dry analytical element containing a creatine kinase activator to such measurement with an element lacking such as activator.

Figure 1:
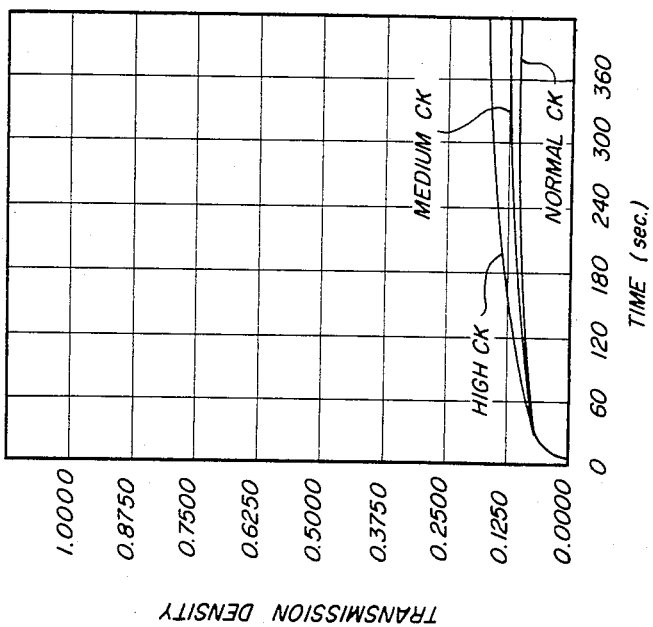

Two types of dry analytical elements were prepared as described in Example 2, except that a Control element contained no creatine kinase activator. The other type contained about 0.54 g/m$^2$ of N-acetylcysteine. Each type of element was spotted with samples from the serum pools of Examples 3-8 (i.e. having normal, medium and high creatine kinase activity) and the rates of creatine kinase activity were then measured. FIG. 1 is a plot of the observed spectrophotometer transmission density vs. time for the Control elements for all three levels of creatine kinase activity. FIG. 2 is a similar plot for elements of this invention containing activator. The increased activity of creatine kinase observed with the elements of this invention is evident from these figures.

The invention has been described in detail with particular reference to preferred embodiments thereof, but it will be understood that variations and modifications can be effected within the spirit and scope of the invention.

What is claimed is:

1. A composition for the quantification of creatine kinase in an aqueous liquid, said composition comprising:
    (a) creatine phosphate;
    (b) adenosine diphosphate;
    (c) glycerol;
    (d) glycerol kinase;
    (e) α-glycerophosphate oxidase;
    (f) a colorimetric indicator composition comprising a chromogen; and (g) a mercapto-containing creatine kinase activator which is present in encapsulated form or at a concentration such that it will not interfere with said colorimetric indicator composition.

2. The composition of claim 1 wherein said colorimetric indicator composition comprises a substance having peroxidative activity.

3. The composition of claim 2 wherein said peroxidative substance is peroxidase.

4. The composition of claim 2 wherein said chromogen is a material capable of undergoing a colorimetric change in the presence of a peroxide and said peroxidative substance.

5. The composition of claim 1 wherein said chromogen is a dye-forming substance.

6. The composition of claim 5 wherein said chromogen is a leuco dye.

7. The composition of claim 1 which is useful in a solution assay for creatine kinase wherein said creatine kinase activator is present in an amount less than about 0.2 mM based on final assay volume.

8. The composition of claim 1 wherein said mercapto-containing compound is N-acetylcysteine.

9. The composition of claim 1 containing an electron acceptor.

10. An analytical element for detecting creatine kinase, said element comprising: creatine phosphate; adenosine diphosphate; glycerol; glycerol kinase; α-glycerophosphate oxidase; a colorimetric indicator composition comprising a chromogen; and a mercapto-containing creatine kinase activator which is present in encapsulated form or in a location such that it does not interfere with said colorimetric indicator composition.

11. An analytical element for detecting creatine kinase, said element including a support and, in fluid contact, first and second zones; and said element comprising:
creatine phosphate; adenosine diphosphate; glycerol; glycerol kinase; α-glycerophosphate oxidase; a colorimetric indicator composition comprising a chromogen; and a mercapto-containing creatine kinase activator,
said first zone containing said colorimetric indicator composition, and said second zone containing said creatine kinase activator.

12. The element of claim 11 wherein said colorimetric indicator composition comprises a substance having peroxidative activity.

13. The element of claim 12 wherein said chromogen is a material capable of undergoing a colorimetric change in the presence of a peroxide and said peroxidative substance.

14. The element of claim 13 wherein said peroxidative substance is peroxidase.

15. The element of claim 11 wherein said first zone is adjacent said support.

16. An analytical element for detecting creatine kinase, said element including a support and, in fluid contact, first and second zones; and said element comprising:
creatine phosphate; adenosine diphosphate; glycerol; glycerol kinase; α-glycerophosphate oxidase; a colorimetric indicator composition comprising a substance having peroxidative activity, and a chromogen; and N-acetylcysteine,
said first zone containing said colorimetric indicator composition, and said second zone containing N-acetylcysteine.

17. The element of claim 16 wherein said N-acetylcysteine is present in said second zone at a coverage of up to about 2 g/m$^2$.

18. An analytical element for detecting creatine kinase, said element including a support having thereon, in order from said support and in fluid contact with each other,
a registration zone containing α-glycerophosphate oxidase and a colorimetric indicator composition comprising a substance having peroxidative activity, and a chromogen;
a reagent zone containing creatine phosphate, adenosine diphosphate, glycerol and glycerol kinase; and
an isotropically porous spreading zone containing a mercapto-containing creatine kinase activator wherein the zones are positioned in a manner such that one is superimposed on the other.

19. The element of claim 18 wherein said colorimetric indicator composition comprises peroxidase and a leuco dye which is oxidized in the presence of hydrogen peroxide and peroxidase.

20. A method for the quantification of creatine kinase in an aqueous liquid, said method comprising the steps of:
(A) incubating a sample of said liquid in the presence of less than about 0.2 mM of a mercapto-containing creatine kinase activator to activate creatine kinase;
(B) contacting
(1) a sample of said activated liquid sample, and
(2) reagents which effect in the presence of a creatine kinase-containing liquid, an ordered sequence of reactions wherein:
(a) creatine phosphate and adenosine diphosphate react in the presence of creatine kinase to form creatine and adenosine triphosphate;
(b) glycerol is phosphorylated in the presence of glycerol kinase and adenosine triphosphate to form L-α-glycerophosphate; and
(c) L-α-glycerophosphate is oxidized in the presence of α-glycerophosphate oxidase and a colorimetric indicator composition to produce an optical density change; and
(C) quantitatively detecting the rate of said change.

21. A method for the quantification of creatine kinase in an aqueous liquid, said method comprising the steps of:
(A) contacting in an aqueous medium and in the presence of an electron acceptor
(1) a sample of said liquid, and
(2) a reagent composition comprising:
(a) creatine phosphate;
(b) adenosine diphosphate;
(c) glycerol;
(d) glycerol kinase;
(e) α-glycerophosphate oxidase;
(f) a colorimetric indicator composition comprising a chromogen; and
(g) a mercapto-containing creatine kinase activator which is present in encapsulated form or at a concentration such that it will not intefere with said colorimetric indicator composition,
to produce an optical density change; and
(B) quantitatively detecting the rate of said change.

22. The method of claim 21 wherein said colorimetric indicator composition comprises a leuco dye and a substance having peroxidative activity.

23. The method of claim 21 wherein said creatine kinase activator is N-acetylcysteine.

24. A method for the quantification of creatine kinase in blood serum, said method comprising the steps of:
(A) contacting in an aqueous medium and in the presence of oxygen
  (1) a sample of said blood serum, and
  (2) a reagent composition buffered to a pH of between about 6 and about 9 and comprising:
    (a) creatine phosphate;
    (b) adenosine diphosphate;
    (c) glycerol;
    (d) glycerol kinase;
    (e) α-glycerophosphate oxidase;
    (f) a colorimetric indicator composition comprising peroxidase and a chromogen which provides quantifiable colorimetric change in the presence of hydrogen peroxide and peroxidase; and
    (g) a mercapto-containing activator for creatine kinase, which activator is present in an amount which renders said activator substantially inert to said colorimetric indicator composition,
  to produce a quantifiable colorimetric change; and
(B) quantitatively detecting the rate of said colorimetric change.

25. The method of claim 24 wherein said mercapto-containing activator is N-acetylcysteine present in an amount of less than about 0.2 mM as measured in the final assay solution.

26. A method for the quantification of creatine kinase in blood serum, said method comprising the steps of:
(A) contacting, in the presence of oxygen, a sample of said blood serum and an analytical element, said element including a support and, in order from said support and in fluid contact with each other,
  a registration zone containing α-glycerophosphate oxidase, peroxidase and a leuco dye which is oxidized in the presence of hydrogen peroxide and peroxidase;
  a reagent zone containing creatine phosphate, adenosine diphosphate, glycerol and glycerol kinase; and
  an isotropically porous spreading zone containing a mercapto-containing creatine kinase activator, to produce a quantifiable colorimetric change; and
(B) quantitatively detecting the rate of said colorimetric change.

* * * * *